United States Patent [19]

Fite et al.

[11] 4,209,693
[45] Jun. 24, 1980

[54] SURFACE IONIZATION MONITOR FOR PARTICULATES AND METHOD

[75] Inventors: Wade L. Fite; Richard L. Myers, both of Pittsburgh, Pa.

[73] Assignee: Extranuclear Laboratories, Inc., Pittsburgh, Pa.

[21] Appl. No.: 930,360

[22] Filed: Aug. 2, 1978

Related U.S. Application Data

[63] Continuation-in-part of Ser. No. 711,231, Aug. 3, 1976, Pat. No. 4,093,855, which is a continuation of Ser. No. 465,163, Apr. 29, 1974, Pat. No. 3,973,121, which is a continuation-in-part of Ser. No. 319,442, Dec. 29, 1972, Pat. No. 3,808,433.

[51] Int. Cl.² .................................. G01N 27/78
[52] U.S. Cl. .................................... 250/251; 250/425
[58] Field of Search ............ 250/281, 282, 283, 292, 250/251, 423 R; 356/222; 324/96

[56] References Cited

U.S. PATENT DOCUMENTS

| | | | |
|---|---|---|---|
| 3,300,640 | 1/1967 | Eubank | 250/251 |
| 3,336,475 | 8/1967 | Kilpatrick | 250/425 |
| 3,433,944 | 3/1969 | George | 250/251 |
| 3,484,603 | 12/1969 | Bloom | 250/251 |
| 3,808,433 | 4/1974 | Fite et al. | 250/251 |

*Primary Examiner*—Bruce C. Anderson
*Attorney, Agent, or Firm*—Mason, Mason and Albright

[57] ABSTRACT

A method and apparatus for monitoring particulates which are borne by a surrounding gaseous medium, such as found in smokestack or the like, through interception of the particulates by a hot filament having a bias potential in the range of about 100 to 1000 volts whereupon each particulate decomposes into a burst of ions which is collected by a nearby electrode at ground potential, by counting those bursts which produce a predetermined total charge and, at the same time, measuring the DC electric current produced by the bursts and other ion exchange between the hot filament and the electrode. The filament operates at a temperature level wherein infrared and visible radiations are emitted, such radiations being monitored by a phototransistor which receives the radiations. The electrical signal from the phototransistor is employed in a feedback loop whereby the power to the filament is either increased or decreased to maintain the detected radiation level and therefore the filament temperature at a prescribed value.

16 Claims, 14 Drawing Figures

SURFACE IONIZATION MONITOR FOR PARTICULATES AND METHOD

RELATED APPLICATIONS

This application is a continuation-in-part of application Ser. No. 711,231 filed Aug. 3, 1976 U.S. Pat. No. 4,093,855 which is a continuation application of application Ser. No. 465,163 filed Apr. 29, 1974 now U.S. Pat. No. 3,973,121, which, in turn, is a continuation-in-part application of application Ser. No. 319,442 filed Dec. 29, 1972, now U.S. Pat. No. 3,808,433.

BACKGROUND OF THE INVENTION

The instant invention relates to an industrial instrument and method for monitoring particulate matter which is borne in the gaseous medium of a stack, duct or the like with improved sensitivity and selectivity of detection.

Presently stacks, ducts and the like for industry are frequently monitored by optical transmissometers and nephalometers which measure the concentration of particles in a gaseous fluid by the analysis of a light beam transmitted through or reflected by the fluid. However, there are certain problems which arise wherein optical methods are not sufficiently accurate such as in a low-opacity stack which even during a crisis situation may not contain sufficient material to produce a reliably measurable opacity; in a process which produces particulates too small for optical scattering and absorption, or where the particles have unfavorable indices of refraction for optical effects; or in a stack containing both harmful and harmless emissions, both of which actuate optical devices.

The inventors in U.S. Pat. No. 3,808,344 disclosed methods and types of apparatus for the detection of airborne particulate matter wherein a particle strikes a hot surface and emits a burst of many ions which are detected electrically by means of their charges. In such invention the air was induced to move in a path containing the hot surface with the particles thus transported to the surface by means of a pump or fan. In certain industrial applications, particularly those involving movement of gas or air in a stack or duct, the hot surface may be placed directly into the flow—whereby the gas movement transports particles to the hot surface. The hot surface is normally a heated wire or ribbon which is operated at a temperature whereby infrared and visible radiation is emitted. The passage of gaseous fluid in which particulate matter is suspended over the hot surface tends to cool same. The power requirement for keeping the hot surface at a proper operating temperature is dependent on the rate of cooling by the passing gaseous fluid. Still further, variations in flow produce variations in the rate of cooling of the filament and, with a given or steady power input which heats the surface, the temperature is subject to variations with airflow variations. Yet further, with long periods of use, the hot surface is slowly oxidized and, if in the form of a wire filament which is heated by ohmic heating, as is often the case, the wire suffers a reduction in diameter. With such reduction, the resistance of the filament is increased which requires a change in the power level if the radiation and hence the temperature, from the filament is to remain constant.

It will thus be understood that a need exists for an instrument which can be utilized in an industrial environment which has the sensitivity and selectivity necessary for the measurement of gaseous borne particulates found in industrial applications, which is not to be adversely affected by variable gaseous flow rates and temperatures, and which maintains the ability to provide a constant measurement irrespective of operative influences which tend to cause changes in the accuracy of the apparatus with age.

SUMMARY OF THE INVENTION

The apparatus and method of surface ionization monitoring for particulates as disclosed herein provides a means for the monitoring of particulates in stacks and ducts which does not require the withdrawal of gas for external analysis and which is beyond the capacity of optical methods for in situ monitoring through the ability to detect particles smaller than the wave length of light and by having a high sensitivity to caustic compounds, metallic fumes and fly ash relative to water mist, soot and products of clean combustion.

The invention consists of two units. The first is an in-stack probe which is mounted directly onto an industrial stack or duct with its sensitive element at the location monitoring is desired, said sensitive element comprising a heated surface and an adjacent ion collector electrode, protruding into the stack or duct for in situ monitoring. The second is an enclosed control unit which is mounted for convenient access by personnel such as near the base of the stack or along a walkway, the control unit and in-stack probe being connected by electrical wiring in a protected conduit. Both are capable of withstanding hostile industrial environments. The in-stack probe includes electronic circuitry for processing signals for transmission to the control unit. Output signals from the control unit may be to a plant control center where data may be recorded and used to activate alarms, as desired. Maintenance involves only the replacement of the sensitive element (the filament) at intervals which may range from several weeks to several months depending upon application. The invention provides, in baghouse monitoring, rapid detection and identification of a defective bag compartment. In precipitator installations, the efficiency of a precipitator is constantly monitored. In addition, it provides a means for immediately detecting a ruptured tube in a heat-exchange system. The monitoring is such that it provides a real-time immediate response, a high sensitivity for particulates and a low sensitivity for mist in wet stacks. Still further, the instrument, and method of the invention, provide a high sensitivity in low-opacity stacks. The invention is advantageously utilized with two information channels which monitor small as well as large particles.

The invention operates by being placed in a location such as an industrial stack where air borne or gas borne dust particles strike a hot filament through inertial deposition from the moving gas whereupon the particles decompose, and transfer some of their atomic and molecular constituents to the surface. Then by a process known as surface ionization, the atomic and molecular constituents which have low ionization potentials are readmitted from the surface as positively charged ions; the entire process—decomposition of the particle and production of the ions—takes only a few micro seconds. The arrival of the particle is registered by a burst of thousands to millions of ions, depending on the particle size and chemical composition. The burst of ions is collected on a nearby electrode producing an electrical current pulse, which is electronically processed by two separate channels. First the total ion current provided by the pulse is added to the ion current carried by all other pulses, producing a DC signal which gives an indication of the total ionizable material being detected. Second, the magnitude of each pulse is analyzed and the number per second of pulses larger than a preset value is displayed as a count rate and represents a concentration of particles having sizes above a predetermined value.

By using means which is responsive to the infrared or visible radiation or both emitted from a hot surface, such radiation being detected by a light detector either directly, or indirectly via transmission through a light pipe, the power for heating the filament is increased or decreased in response to the electrical signal from the light detector which is employed in a feedback loop so that the detected radiation level and therefore the filament temperature is maintained at a prescribed value.

Other objects, adaptabilities and capabilities of the invention will be understood by those skilled in the art as the description progresses, reference being had to the accompanying drawings in which:

DESCRIPTION OF THE PREFERRED EMBODIMENTS

Referring to FIGS. 1 through 5, the monitoring assembly, referred to in the art as a "probe" and designated generally by reference numeral 12, comprises a stainless steel housing cylinder 14 which is provided with a ring member 15 on its outboard end rigidly attached thereto and which mounts an outboard cover plate 16 by means of six bolts 17 which are received through bores spaced apart by 60° around the periphery plate 16 and by corresponding threaded apertures provided in ring member 15. An O-ring 20 is received in an outboard circumferential slot in ring member 15 to provide a hermetic seal between plate 16 and ring member 15. Onto the inboard side of cover plate 16 is mounted, via electrical stand offs 16a, a preamp circuit card 11 which provides the electronic amplification necessary for operation of the probe in a remote location. Also mounted on cover plate 16 is a plate 13 on which are mounted two terminal barrier strips 18a and 18b which receive and secure electrical connectors from outside the probe. Further, plate 13 contains a screw-on connector 19 which allows detachable electrical connections to be made to the components on the inboard end of housing 14. Rigidly connected to the inboard side of housing 14 is a stack flange 21 which contains a vertically disposed radial bore 22. A mounting nipple 24 is rigidly connected on its inboard side to stack flange 21 and surrounds for a short distance a support tube 25 which shields and provides support for a light tube 26, a pair of filament conductor rods 27 and 28 and an electrode conductor rod 30, said rods 27, 28 and 30 being carried by ceramic tubes 23.

Figures 1, 2A, 3, 4:
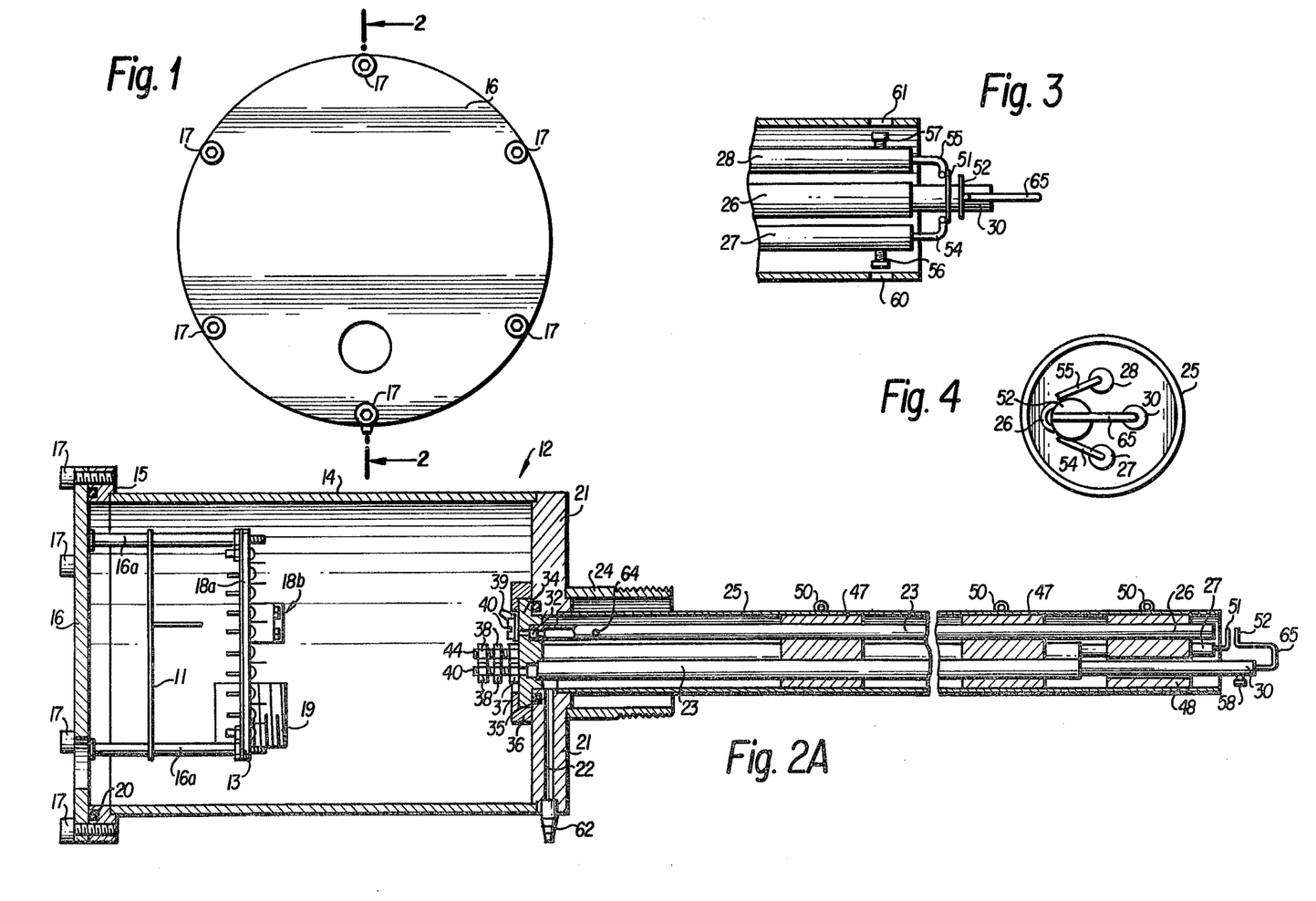
FIG. 1 is an end view of a monitoring device in accordance with the invention.
FIG. 2A is a side elevation sectional view of the invention taken on lines 2—2 of FIG. 1.
FIG. 3 is a fragmentary sectional view as seen from above the inboard end of the invention.
FIG. 4 is an inboard end view of the invention.
Figure 2B:
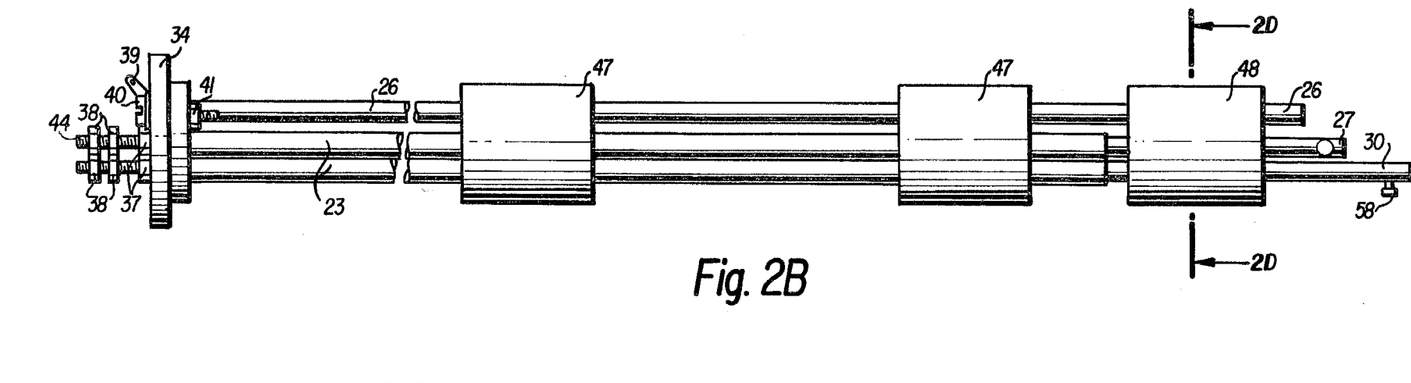
FIG. 2B is a detailed view of interior parts of probe shown in FIG. 2A.

On the inboard end of light tube 26 a phototransistor 32 is received in and supported by a feed-through element 34 which also receives and provides support for rods 27, 28 and 30 and tubes 23. Between feed-through element 34 and stack flange 21 is a circumferential groove which receives an O-ring member 35. A nylon nut 37 is received about the threaded end of each of conductor rods 27, 28, and 30 to affix rods 27, 28, and 30 securely to feed-through element 34, and further stainless steel nuts 38 are placed onto the threaded end of said conductor rods to enable electrical connections to be made to a matching screw-on connector (not shown for clarity) which mate with screw-on connector 19. Phototransistor 32 possesses two conductor wires each of which passes through apertures on feed-through element 34 as shown, whereupon these conductor wires are fastened to wiring lugs 39 which are themselves fastened to feed-through element 34 by nylon screws 40 which, in turn, are fastened into holes in feed-through element 34 by nylon nuts, 41. Wiring lugs 39 also are used to fasten other conductor wires whereby electrical connection between conductor wires emanating from phototransistor 32 and the above-mentioned screw-on connector which mates with screw-on connector 19 are provided.

Figure 2C:
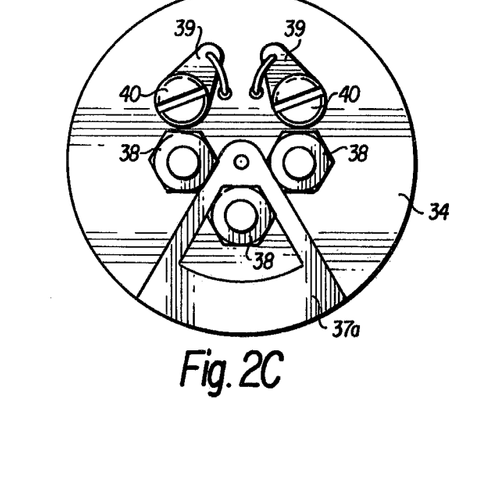
FIG. 2C is an end view illustrating the guard ring for the feedthrough shown in FIGS. 2A and 2B.

To ensure that no electrical current leakage occurs across the surface of feed-through element 34 from filament rods 27 and 28 to ion collector rod 30, an electrically grounded conducting surface 37a known to all skilled in the art as a "guard ring" as applied to both sides of feed-through element 34 in the manner shown in FIG. 2C. The surface 37a is composed of a material, having a brand name, "Silverprint" or any other similar material known to those skilled in the art. To provide that "guard ring" surface 37a on each side of feed-through element 34 are electrically connected, a small hole is drilled through the center of feed-through element 34 and conducting surface 37a is continued on the inside surface of the hole; thereafter the hole is sealed closed. Support tube 25 contains a pair of spacer plugs 47 which are of identical construction having an outside circumference whereby they are received snugly yet slideably within tube 25 and each is provided with a plurality of apertures to receive carriers 23 for metal rods 27, 28 and 30 and light tube 26. Spacer plugs 47 are affixed within tube 25 respectively by a pair of setscrews 50.

Figure 2D:
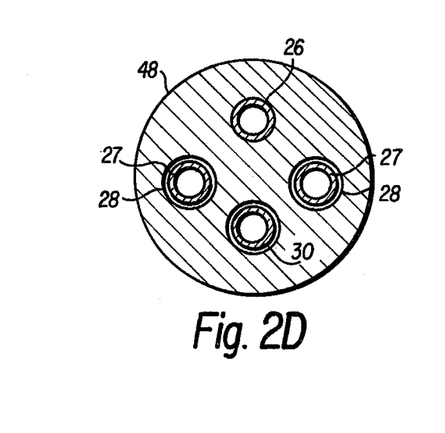
FIG. 2D is a sectional view taken on lines 2D—2D of FIG. 2B showing the purge air baffle in the probe assembly.

In stacks and ducts containing moist air or dust which is electrically conducting, there is provided a third spacer plug 48, as shown in section in FIG. 2D substantially identical to the other two spacer plugs 47 with the exception that spacer plug 48 does not provide support for ceramic tubes 23 or for filament rods 27 and 28 or for collector rod 30 and is spaced therefrom. Spacer plug 48, which may be considered a "purge air baffle" provides continuous air gaps between the various ceramic rods 23 whereby moisture or dust cannot be deposited onto the ceramic rods 23 and cause an electrically conducting path to be created. Purge air baffle 48 is positioned within support tube 25 at a position beyond the ends of ceramic rods 23; hence, cylindrical air gaps are created between the holes through baffle 48 and the rods 27, 28, and 30 which project beyond the inboard ends of ceramic rods 23. Thus these air gaps, as well as the more inboard air spaces between ceramic rods 23, are kept clean and dry by passing clean and dry air through support tube 25 in the inboard direction relative to the stack in a manner to be described.

Figure 10:
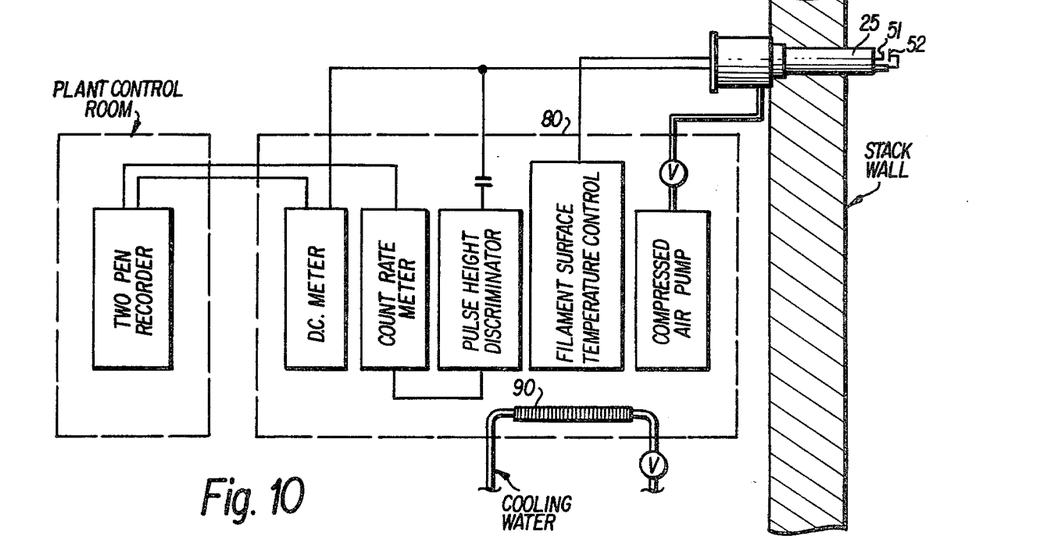
FIG. 10 is a diagrammatic representation showing components of the invention installed on a stack.

The sensitive element in the monitoring device is a hot surface in the form of a wire filament 51 and an adjacent collector electrode 52 at which ions produced at filament 51 are collected and thereafter registered electrically. In the embodiment shown, this assembly is located in the stack proper, extending only a short distance beyond the end of the protective sheath consisting of support tube 25 which protrudes into the stack as shown in FIG. 10. The filament 51, in this embodiment, is platinum or an alloy composed primarily of platinum. It has a 0.015" diameter and is mounted on two rigid supports comprising stainless steel rods 54 and 55. As seen in FIG. 3, filament 51 may be easily removed, or replaced or adjusted by loosening the setscrews 56 and 57 in rods 27 and 28 through access holes 60 and 61 defined in the sides of the support tub 25 at its inboard end. Electrode 52 is supported by a stainless steel rod 65 received by an end bore in rod 30 and secured in place by a setscrew 58. Viewing filament 51 is light tube 26 which transmits the brightness of filament 51 to a monitoring phototransistor 32 mounted in feed-through element 34 at the outboard end of the support tube 25.

Stack flange 21 is fitted with a hose connector 62 for the receipt of dry air for transmission into the outboard base of support tube 25 to prevent condensation within tube 25 and to ensure that the interior of light tube 26 is kept clean. For the latter purpose, an aperture 64 is defined in the outboard end of light tube 26 near transistor 32. Further openings for the passage of air in tube 25 are provided in the two spacer plugs 47. This dry air also provides sufficient cooling for support tube 25 and components therein whereby the support tube 25 may be used successfully in stacks with interior temperatures approaching 600° F. However where the outboard base portion of support tube 25 may raise to temperatures above 150° F., the provision of an insulation heat shield sleeve surrounding tube 25 may be utilized to advantage.

Figures 5, 7, 8:
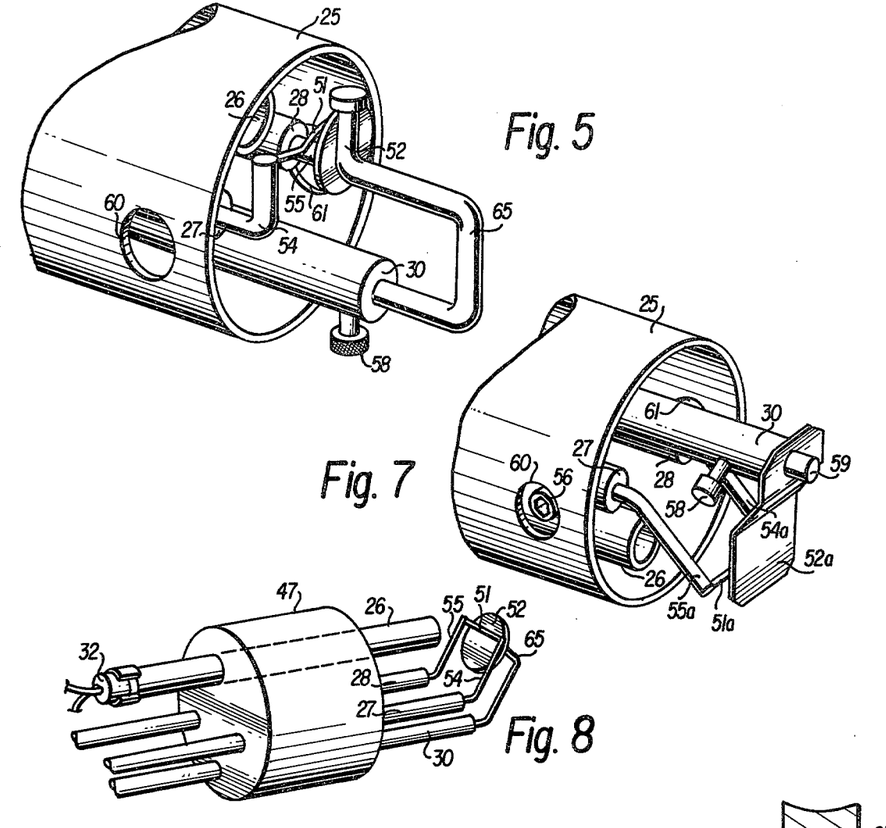
FIG. 5 is a perspective of the inboard end of the invention.
FIG. 7 is a detailed perspective view of an alternate embodiment of the inboard probe in accordance with the invention.
FIG. 8 is a diagrammatic view which illustrates the relationship of the photocell or phototransistor which monitors the emission of the hot filament.

FIG. 7 is similar to FIG. 5 showing, however, a different embodiment wherein the electrode plate 52a is applied directly to rod 30 by a shaft 59 affixed thereto and received in an end bore of rod 30 wherein it is rigidly secured by setscrew 58. Filament 51a is positioned adjacent plate 52a by support rods 54a and 55a secured to rods 28 and 27 in the same manner as rods 54 and 55.

FIG. 8 illustrates diagrammatically the sensitive elements of the probe. Thus it will be noted that the components are positioned by the spacer insulating plug 47 (actually two as shown in FIGS. 2 and 4). Filament supports 54 and 55 are received in bores in the ends of rods 27 and 28 respectively. Ions are collected at the ion collecting electrodes 52 which is supported by stainless steel rod 65. A phototransistor 32 is mounted in a well in the feed-through 34 (not shown in FIG. 8) at the end of the light pipe 26 which directly views the hot filament 51. The MRD-300 phototransistor is found to be a suitable light detector although other suitable types of light or radiation detectors may also be used. The light tube or pipe 26 can be either a hollow glass tube or a solid glass tube or a hollow tube of other material which reflects well at the interior surface. In the preferred embodiment, a hollow glass tube is utilized as the light pipe. Other types of light pipes may also be used such as fiber optics light pipes as will be understood by those skilled in the art.

Figure 9:
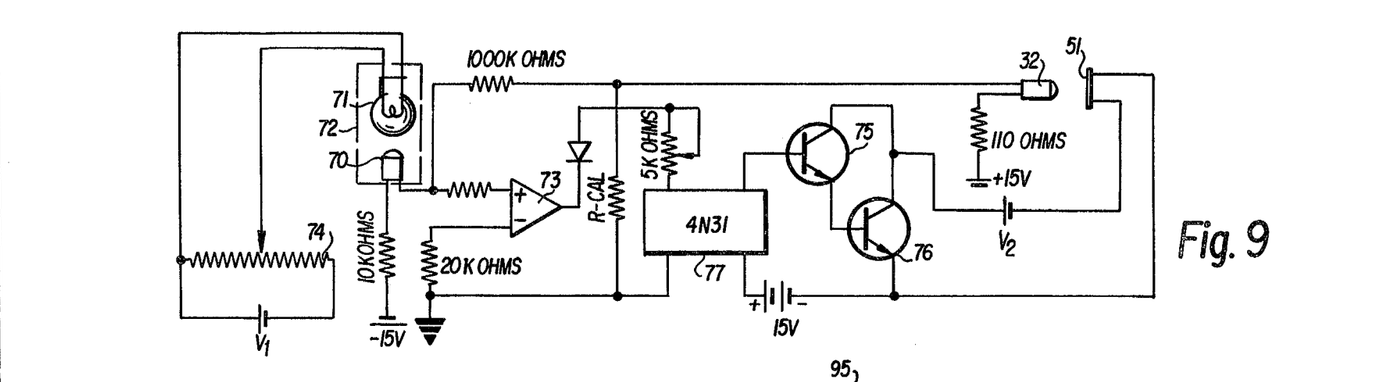
FIG. 9 is the circuit for controlling the amount of radiation from the hot filament.

A preferred method of controlling the filament temperature is shown in simplified form in the wiring diagram of FIG. 9. The filament 51, the temperature of which is to be controlled, is viewed by phototransistor 32. A similar second phototransistor 70 views a filament which is in a vacuum enclosed in light bulb 71 with the light bulb and phototransistor being enclosed in a black housing 72. The brightness of the filament in light bulb 71 is controlled by a circuit which controls the voltage $V_1$ which includes a variable resistor 74.

The remaining portion of the circuitry serves the function of comparing the brightness of filament 51 and the filament light bulb 71 and to adjust the voltage heating of the filament 51 so that the outputs of the two phototransistors 32 and 70 are equal. This is accomplished by first providing that the current from one of the phototransistors (70) is a negative current whereas that of the other (32) is a positive current. These two currents are both fed into the plus input of an operational amplifier 73 which can be a type identified by the symbol LHOO22CD. Inasmuch as the currents are opposite in polarity, when the two phototransistor signals have been matched there is no net current in the operational amplifier; when one of the currents is greater than the other, the net unbalance of the currents causes the operational amplifier 74 to drive a double transistor circuit consisting of two transistors 75 and 76 which may be of a type identified by symbol 2N3055 and which regulate the amount of voltage from a voltage source $V_2$ which is applied directly to the negative lead to filament 51 and, via transistors 75 and 76 without direct electrical connection. This permits filament 51 to be referenced to a bias potential other than the referenced potential of the operational amplifier 74 as is frequently required by the particle detector. In the preferred embodiment shown in FIG. 9 a light emitting diode and phototransistor combination 77 is employed for such purpose. Such combination has the commercial symbol of 4N31.

Because the geometries in which the two phototransistors view the two filaments differ in general, and also because the variations between individual phototransistors, the circuitry includes a provision for varying the fraction of current produced in phototransistor 32 viewing the filament 51 by diverting a portion of the output current through a resistor designated as R-Cal. By this means, the filament within light bulb 71 may be adjusted to a temperature within the general temperature range at which the filament 51 operates. The R-Cal value is selected whereby filament 51 operates at the same temperature as determined by direct viewing of the filament 51 with an optical pyrometer. In general, the value of the R-Cal is in the range of between 5,000 and 50,000 OHMs.

If the changes of the cooling rate cause temperature and therefore brightness variations of filament 51, the circuitry automatically adjusts the voltage to filament 51 so as to restore its original temperature and brightness. The circuitry also provides for the changing of the temperature at which filament 51 is to operate. This is accomplished by varying the setting of the potentiometer 74 which causes the brightness of the filament and light bulb 71 to change and thus causes a net current flow to the plus input to the operational amplifier 73. The circuitry then causes voltage to filament 51 to change until the brightness of filament 51 again matches that of the filament in light bulb 71 as determined by comparison of the phototransistor outputs.

Figure 6:
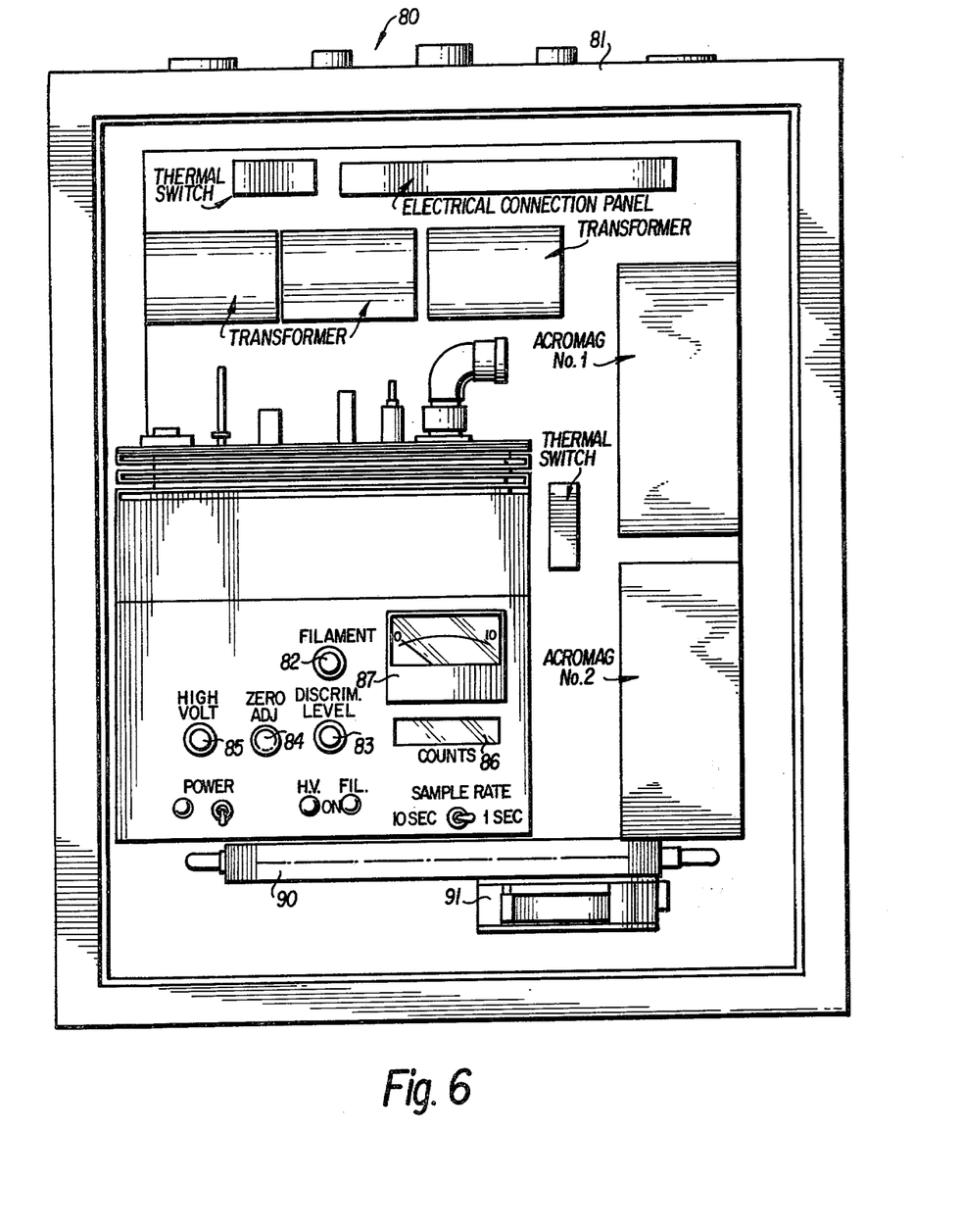
FIG. 6 is an elevational view of the control unit of the invention which is situated within a weathertight housing therefor.

As seen in FIG. 6 and illustrated diagrammatically in FIG. 10, a control unit 80 is housed in a weathertight enclosure 81 and available to an operator are filament temperature controls 82, pulse height discriminator controls 83 which determine the lower size cutoff point for particulates to be registered as counts and a zero adjustment control 84, for the DC ion current level. The bias voltage on filament 51 is adjusted by a voltage control 85. An ion current meter 87 shows the DC signal and a digital panel meter 86 displays the count rate which provide the operator with immediate information on the instrument's output without having to refer to chart recorders in the control room. Once the controls are set at the time of installation or servicing, control unit 80 requires no further attention. Also seen in FIG. 6 is a water-cooled coil 90 in combination with a fan 91 which is useful when the control unit 80 is mounted in an extremely hot location. In lieu thereof, the units may be air cooled or provided with electrical refrigeration cooling.

The count rate recorded by a digital panel meter 86 and elsewhere, if desired, records the number of pulses per second generated by particles received by filament 51, each pulse occurring with arrival at the surface of filament 51 of a particle having a size which is greater than the value determined by the setting of the pulse height discriminator control 83. The count rate is thus a measure of the concentration of the larger particulates in the stack. An internal rate meter converts the separate particle counts into an analog count rate signal for direct display on a recorder.

The DC ion current as displayed on the meter 87 is the total electrical charge carried by ions produced from particles received on the filament 51 averaged over a period of time. Inasmuch as both the larger and smaller particles contribute to the total ion current, such output is a measure of the total mass concentration in particles of all sizes.

Both outputs may be presented at a plant control room as 4 to 20 milliampere signals.

Figure 11:
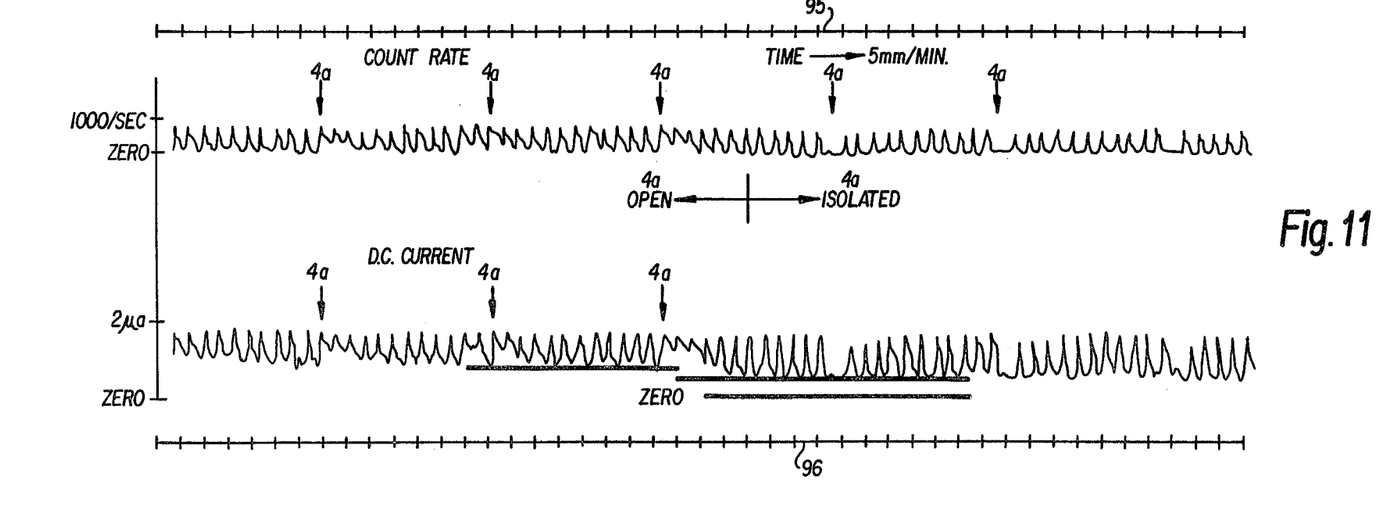
FIG. 11 depicts baghouse signal outputs from the invention wherein one of the bag modules is defective.

The recorded tracing in FIG. 11 shows both the count rate (the upper trace 95) and the DC current count (the lower trace 96) when the invention was operated on a baghouse stack at a plant manufacturing dry granular material which contained sodium compounds as constituents. The baghouse contained twelve modules, each being reverse air-pulsed every six minutes. Sequential reverse pulsing produced a puff of material in the stack every thirty seconds.

It will be noted that at the left of the tracing are signals in one of the modules (designated Module 4a) was leaking. Midway in the tracing, such module was isolated and the right half of the chart shows a normal output signal with a normal baghouse operation.

It is to be seen that the pulses associated with a defective module are characteristically different from a normal pulses in both information channels. Further, in normal operation, the count rate between the pulses falls to zero whereas the DC ion current does not. Although the bags are effective in trapping particulates above about one micron in diameter, the level for which the pulse height discriminator was set, small particulates penetrate the bag fabric at all times. Finally, it is to be seen that the DC ion base level is markedly decreased with isolation of the defective module.

Through correlation of the electrical pulses with the baghouse pulsation sequence, immediate identification of the module 4a as the one to be isolated is determined.

Although the preferred embodiment of the invention as described herein, it is to be understood that the invention is capable of other adaptations and modifications within the scope of the appended claims.

Having thus described our invention, what we claim as new and desire to secure by Letters Patent of the United States is:

1. A method of monitoring particulates borne in a surrounding moving gaseous medium within a stack or duct which is at least at about atmospheric pressure which comprises the interception of said particulates in situ by a hot filament extending therein, causing said particulates to decompose and produce bursts of ions, collecting said ions by a nearby electrode, providing a bias potential differential between said electrode and said filament of about one hundred or more volts, counting said bursts having a predetermined total charge and measuring the electrical current produced by ions flowing from said filament to said electrode.

2. A method in accordance with claim 1, wherein for the purpose of counting said bursts, discrimination is provided to separate small bursts of ions and more intense bursts.

3. A method in accordance with claim 2, wherein the only bursts counted are those caused by particulates having a diameter of about one micron or more.

4. A method in accordance with claim 2, wherein said bursts which are counted are caused by macromolecular ions of 100 AMU or greater.

5. A method in accordance with claim 1, wherein said filament is maintained at a temperature of 800 to 1500 degrees Centigrade.

6. A method in accordance with claim 1, wherein said filament is maintained at a positive voltage in the range of 100 to 1000 volts with respect to the ion collector.

7. A method in accordance with claim 6, wherein said voltage is a negative voltage.

8. An apparatus for monitoring particulares borne in a surrounding moving gaseous medium in a stack or duct which comprises a probe housing which is located at least in part in said stack or duct through which said gaseous medium flows, a hot filament extending from said housing and into said gaseous medium whereby it intercepts particulates borne therein, said filament being adapted to cause said particulares to decompose and produce by surface ionization a burst of ions to be emitted from said hot filament upon each said decomposition, an electrode near said hot filament adapted to receive said bursts of ions, means for maintaining a bias potential difference between said hot filament and said electrode of at least about one hundred volts, and means for registering each said burst of a predetermined total charge.

9. Apparatus in accordance with claim 8, wherein discrimination means is provided to register only bursts from particulate matter having a diameter of one micron or more.

10. Apparatus in accordance with claim 8, including means for measuring the electrical current produced by the flow of ions between said filament and said electrode.

11. An apparatus in accordance with claim 8, including Ohmic heating means for heating said filament.

12. Apparatus in accordance with claim 11, wherein said filament is heated to a temperature in the range of 800 to 1500 degrees Centigrade by said Ohmic heating means.

13. Apparatus in accordance with claim 8, wherein said filament and said electrode are spaced apart by a distance of a range of 0.5 to 5.0 millimeters.

14. A method of monitoring particulates borne in a surrounding moving gaseous medium which comprises the interception of said particulates by a hot filament extending from a tubular probe in said medium, causing said particulates to decompose and produce bursts of ions, collecting said ions by a nearby electrode extending from said tubular probe, providing a bias potential differential between said electrode and said filament of about 100 or more volts, counting said bursts having a predetermined total charge, measuring the electrical current produced by ions flowing from said filament to said electrode, and conveying a dry relatively cool gas through said tube for cooling same and for preventing dust and moist gas which is being monitored from entering said tubular probe.

15. An apparatus for monitoring particulates borne in a surrounding moving gaseous medium which comprises a probe housing which is located at least in part in said gaseous medium, a hot filament extending from said housing and to said gaseous medium whereby it intercepts particulates borne therein, said filament being adapted to cause said particulates to decompose and produce by surface ionization a burst of ions to be emitted from said hot filament upon each said decomposition, an electrode near said hot filament to receive said bursts of ions, means for maintaining a bias potential difference between said hot filament and said electrode of at least 100 volts, means for registering each said burst of a predetermined total charge, and in combination with the foregoing apparatus a control unit housing a weather-tight closure which is removed from said probe housing.

16. An apparatus for monitoring particulates borne in a surrounding moving gaseous medium which comprises a probe housing which is located at least in part in said gaseous medium, said housing being connected to a dry air passage for moving comparatively dry air through said housing to prevent condensation from occurring in said housing, a hot filament extending from said housing and to said gaseous medium whereby it intercepts particulates borne therein, said filament being adapted to cause said particulates to decompose and produce by surface ionization a burst of ions to be emitted from said hot filament upon each said decomposition, an electrode near said hot filament adapted to receive said burst of ions, means for maintaining a bias potential difference between said hot filament and said electrode of at least about 100 volts, and means for registering each said burst of a predetermined total charge.

* * * * *